(12) United States Patent
Martinez et al.

(10) Patent No.: US 9,767,526 B2
(45) Date of Patent: Sep. 19, 2017

(54) CLINICAL TRIALS SUBJECT IDENTIFICATION SYSTEM

(75) Inventors: Pedro L Martinez, Boca Raton, FL (US); Nicholas Koutrakos, Delray Beach, FL (US); Joseph A Pores, Boca Raton, FL (US); Ania Clara Rodriguez, Doral, FL (US)

(73) Assignee: HEALTH META LLC, Boca Raton, FL (US)

( * ) Notice: Subject to any disclaimer, the term of this patent is extended or adjusted under 35 U.S.C. 154(b) by 846 days.

(21) Appl. No.: 13/470,045

(22) Filed: May 11, 2012

(65) Prior Publication Data
US 2013/0304484 A1    Nov. 14, 2013

(51) Int. Cl.
| | | |
|---|---|---|
| *G06Q 50/00* | (2012.01) | |
| *G06Q 50/22* | (2012.01) | |
| *G06Q 10/06* | (2012.01) | |
| *G06Q 30/02* | (2012.01) | |
| *G06Q 50/24* | (2012.01) | |
| *G06F 19/00* | (2011.01) | |
| *G06F 21/62* | (2013.01) | |

(52) U.S. Cl.
CPC ........... *G06Q 50/22* (2013.01); *G06Q 10/067* (2013.01); *G06Q 30/0203* (2013.01); *G06Q 50/24* (2013.01); *G06F 19/322* (2013.01); *G06F 19/363* (2013.01); *G06F 21/6263* (2013.01)

(58) Field of Classification Search
CPC ...... G06Q 50/22; G06Q 50/24; G06F 19/363; G06F 19/36
See application file for complete search history.

(56) References Cited

U.S. PATENT DOCUMENTS

| | | | |
|---|---|---|---|
| 6,151,581 A * | 11/2000 | Kraftson et al. | 705/3 |
| 6,839,678 B1 * | 1/2005 | Schmidt et al. | 705/3 |
| 7,251,609 B1 * | 7/2007 | McAlindon et al. | 705/3 |
| 7,711,580 B1 * | 5/2010 | Hudson | 705/3 |
| 2001/0038624 A1 * | 11/2001 | Greenberg et al. | 370/352 |
| 2002/0099570 A1 * | 7/2002 | Knight | 705/2 |
| 2004/0122951 A1 * | 6/2004 | Beck et al. | 709/227 |
| 2004/0127232 A1 * | 7/2004 | Kotzin | H04L 67/18 455/456.6 |
| 2005/0182658 A1 * | 8/2005 | Abraham-Fuchs | G06F 19/327 705/2 |
| 2005/0210015 A1 * | 9/2005 | Zhou et al. | 707/3 |

(Continued)

OTHER PUBLICATIONS

The Insiders Guide to AdWords. https://web.archive.org/web/20090124115131/http://www.google.com/adwords/insider/Insiders_Guide_to_AdWords.pdf Earliest publication date unknown. Archived by Wayback machine on Jan. 24, 2009. Accessed Oct. 25, 2016.*

(Continued)

*Primary Examiner* — Minnah Seoh
*Assistant Examiner* — Jonathan Durant
(74) *Attorney, Agent, or Firm* — Akerman LLP; Mammen (Roy) P. Zachariah, Jr.

(57) ABSTRACT

Matching a subject with a clinical trial includes steps of: collecting patient data associated with the subject; collecting clinical trial data from multiple sources; matching the subject to a clinical trial scheduled in a location accessible to the subject; notifying a health care provider associated with the subject about the clinical trial; and receiving a response.

14 Claims, 11 Drawing Sheets

(56) References Cited

U.S. PATENT DOCUMENTS

| | | | | |
|---|---|---|---|---|
| 2006/0149602 A1* | 7/2006 | Zammit | ............... | G06F 19/363 705/3 |
| 2006/0229916 A1* | 10/2006 | Michelson et al. | ............... | 705/2 |
| 2007/0294354 A1* | 12/2007 | Sylvain | ............... | 709/206 |
| 2010/0250285 A1* | 9/2010 | Shelton | ............... | 705/3 |
| 2010/0332258 A1* | 12/2010 | Dahlke et al. | ............... | 705/3 |
| 2011/0282692 A1* | 11/2011 | Kane et al. | ............... | 705/3 |
| 2012/0158420 A1* | 6/2012 | Lacal | ............... | G06Q 10/00 705/2 |

OTHER PUBLICATIONS

Gordon, Judith S., et al. Successful participant recruitment strategies for an online smokeless tobacco cessation program. Nicotine & Tobacco Research 8.Suppl 1 (2006) S35-S41.*

* cited by examiner

CLINICAL TRIALS SUBJECT IDENTIFICATION SYSTEM

CROSS-REFERENCE TO RELATED APPLICATIONS

None.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of medical information technology, and more particularly relates to the field of information technology related to clinical trials.

BACKGROUND OF THE INVENTION

A clinical trial is a medical research study involving human subjects. Clinical trials are used to determine if a new medical drug (compound), medical device, or medical procedure is safe and effective for human use. Clinical trials are scheduled after successful pre-clinical animal testing. Clinical trials are burdened with expense and inefficiency in the recruitment of subjects. The average number of eligibility criteria used to screen volunteers has risen exponentially over the years, contributing to a decline in volunteers willing to enroll in the trials.

Additionally, the number of required procedures for each clinical trial has risen dramatically in the last several years. This is partly because of the increasing complexity of the studies themselves, and partly because of the mandated safeguards. The increased procedures dissuade volunteers from completing the trials. Because clinical trials involve experimental drugs and procedures, a host of safeguards has been set in place to protect the human subject as much as possible. The Department of Health and Human Services mandates policies to protect the confidentiality and rights of human trial subjects. Standards and guidelines are in place to ensure that the final results that are reported are accurate and credible and that the confidentiality and rights of trial participants are protected. While necessary, this adds a tremendous administrative overhead to an already expensive endeavor.

There is a need for a method to improve the efficiency while reducing the costs of clinical trials.

SUMMARY OF THE INVENTION

Briefly, according to an embodiment of the invention a method of automatically matching a subject with an available clinical trials includes steps or acts of: collecting patient data associated with the subject; collecting clinical trial data from multiple sources; matching the subject to a clinical trial scheduled in a location accessible to the subject; notifying a health care provider associated with the subject about the clinical trial; and receiving a response.

According to another embodiment of the present invention, a method of soliciting a subject for a clinical trial includes steps or acts of receiving a health-related search term provided by the subject; determining a location of the subject; matching the health-related search term to a target keyword from a data store; mapping the target keyword to a medical condition under consideration for a clinical trial; determining that the clinical trial for the medical condition is scheduled in a location accessible to the subject; and serving an announcement to the subject with links to a site with information about the clinical trial.

According to another embodiment of the present invention, a distributed computing system for identifying a subject for a clinical trial includes: a memory with computer-executable instructions stored therein, and a processor device operably coupled with the memory. The computer-executable instructions cause a computer to perform: collecting patient data associated with the subject; collecting clinical trial data from multiple sources; matching the subject to a clinical trial scheduled in a location accessible to the subject; notifying a health care provider associated with the subject about the clinical trial; and receiving a response.

BRIEF DESCRIPTION OF THE SEVERAL VIEWS OF THE DRAWINGS

To describe the foregoing and other exemplary purposes, aspects, and advantages, we use the following detailed description of an exemplary embodiment of the invention with reference to the drawings, in which.

Figure 1:
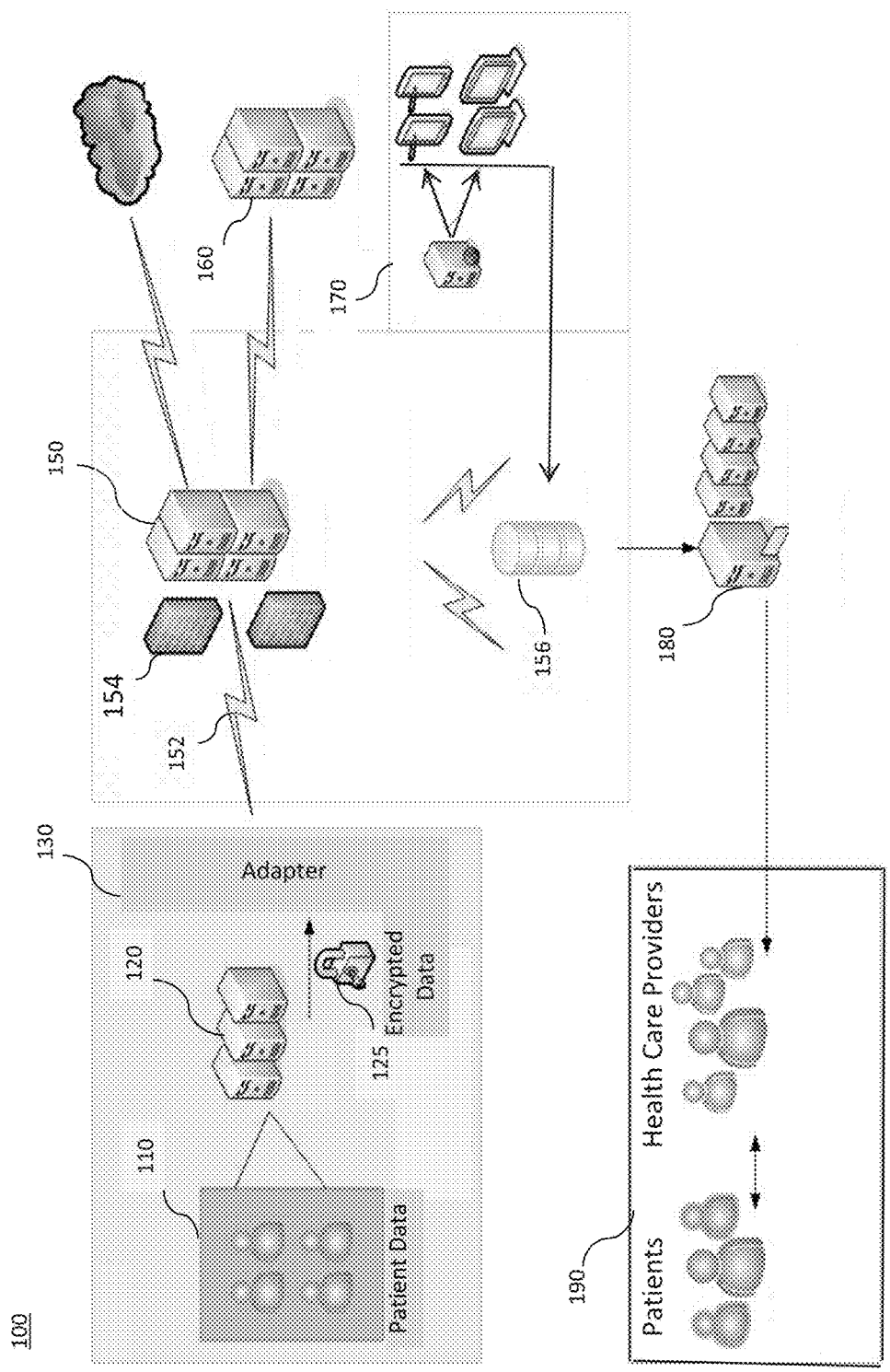
FIG. 1 is a high level block diagram showing an information processing system configured to operate according to an embodiment of the present invention.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

Before describing in detail embodiments that are in accordance with the present invention, it should be observed that the embodiments reside primarily in combinations of method steps and system components related to systems and methods for placing computation inside a communication network. Accordingly, the system components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

We describe an automated clinical trials subject identification system to match subjects with clinical trials. The net effect of this invention is an increased amount of pre-qualified subjects for clinical trials, and a reduction in recruitment costs. This enlarges the statistical base, a requirement for management of population studies. We also accelerate the path to discovery and market, representing millions of dollars per week to pharmaceutical companies.

The present invention will now be described with respect to FIGS. 1 through 12, which are block diagrams and flowchart illustrations of embodiments of the present invention. It will be understood that each block of the flowchart illustrations and/or block diagrams, and combinations of blocks in the flowchart illustrations and/or block diagrams, can be implemented by computer program instructions residing in a computer component.

Referring now to the drawings and to FIG. 1 in particular, there is illustrated an automated clinical trials subject identification system 100, according to an embodiment of the present invention. The system 100 receives input from several sources. One of these sources represents patients who might become subjects for clinical trials. The patients are from geographically distributed regions. This is important for most clinical trials because it assures a better random sampling of the population as a whole.

In one embodiment of the present invention, the patients contact their regional Medical Call Center 120 via phone, Web chat, messaging, and the like, to report on a variety of health conditions. This information can include: a) current and past medical conditions; b) emergencies; c) requests for call backs; d) health questions; and e) medication information. Additionally the patients can provide valuable information about lifestyle, genomics, and environmental factors that add another dimension to their health profile.

By partnering with Call Centers, 120 we leverage the "tech support" paradigm of remote data/voice/video convergence to provide a powerful integrated voice/data/video platform. Patients can access the Call Centers 120 by telephone or through their Web browser using a "click-to-talk" or "chat" feature provided on a website. If a patient is searching the Web seeking information about a health concern, the patient is able to click on an icon or hyperlink on the browser to speak with a call center agent. With this integrated Web search and talk feature, the patient is able to speak with a qualified agent live on-line, without having to go off-line to use the telephone.

The Call Center Database Servers 120 capture the patient data 110 from the voice transaction between the patients and call center staff. The call center 120 agent can "recognize" the caller by a cookie file (or by user login) and see the Web page the user is calling from. This allows the call center 120 agent to intelligently and expeditiously route the call.

We permanently and securely store the data 110 derived from communications with patients in a comprehensive, structured, searchable computer system readable format in the Call Center 120 servers. We provide Health Insurance Portability and Accountability Act (HIPAA) compliance, which is currently mandatory in the management of patient health information. The Call Center servers 120 act as an Electronic Health Record for the patients and the Call Center 120 personnel are able to provide continuity of communications by viewing history and profile information. Additionally, Data Encryption 125 provides secure and HIPAA-compliant electronic information transfers between the Call Center Database Servers 120 and related recipients of information.

The Adapter 130 is operably coupled with the Call Center 120 servers to provide the electronic interface, communications protocol, and management of information transfers to and from the Call Center Servers 120 and the Hub 150. This provides the governance, security, and intelligence of data transfers for integration, synthesis and analysis. The Adapter 130 combines several data sources on-site automatically and securely transmits patient details to the data hub centers 150.

The Hub 150 is operably coupled with the Adapter 130. The Hub 150 is analogous to the central processing unit within a computer. It receives continuous feeds of electronic data from the Call Center Databases 120 and from the Clinical Trials Web sites monitoring database 160. The Hub 150 provides the intelligent matching of subject to clinical trial. With the attributes of an electronic learning system, the Hub 150 refines its search and matching with each transaction. Algorithms are used as the basis for the matching engine; these provide the rules and criteria for information selection and processing.

We provide here exemplary algorithms for zip code proximity search on trials and patients, practices:

$$D=R*(\arccos(\cos(O1)*\cos(O2)*(\text{LatLon2}-\text{LatLon1})+\sin(O1)*\sin(O2),$$

where Longitudes and Latitudes are pre-calculated on look-ups of zip code.

To determine the "value" of various inclusionary and exclusionary factors in the trials data we use a technique called "Weighted Sample Variance" represented by:

$$\sigma^2 = \frac{\sum_{i=1}^{N}(x_i - \mu)^2}{N}$$

$$\sigma^2_{weighted} = \frac{\sum_{i=1}^{N} w_i(x_i - \mu^*)^2}{V_1}$$

where $V_1 = \sum_{i=1}^{n} w_i$, which is 1 for normalized weights.

With the following for specific vectors.

$$W_i = \Sigma_i^{-1}.$$

The weighted mean in this case is:

$$\bar{x} = \left(\sum_{i=1}^{n}\sum_{i}^{-1}\right)^{-1}\left(\sum_{i=1}^{n}\sum_{i}^{-1}x_i\right),$$

and the covariance of the weighted mean is:

$$\sum_{\bar{x}} = \left(\sum_{i=1}^{n}\sum_{i}^{-1}\right)^{-1},$$

Secure Data Relays 152 enable the private and HIPAA compliance of sensitive data transfers to the Hub 150. This is achieved through the combination of secure networks, software security technologies, and process management by the communications services provider. All data collected from partner Call Centers 120 are securely sent to our data processing Hub 150 for matching and notification. All patient and clinical trial matches are stored in the Hub data store 156.

Firewalls 154 (electronic data firewalls) are used to protect, isolate, and manage traffic in and out of the Hub 150. These firewalls 154 use established protocols and security techniques to ensure the authenticity and safety of data.

From the Hub 150, notifications are generated for the patient's health care providers (HCP) indicating a potential qualification for a clinical trial, and could be relayed to patients by their HCP. Notifications are provided by computer generated means, but they can also be relayed by fax, letter, or phone, if need be. The latter methods of transmission may be necessary for the elderly patients. HCP in this context refers to the individual or group responsible for monitoring the health of the patient. Traditionally the HCP was the patient's physician. As health care evolves, the HCP today can be a medical doctor, a physician's assistant, a hospitalist, a doctor of osteopathy, a medical center, clinic, or other. A new direction in medical care is the role of HCPs providing the "Medical Home" for the patient. The Medical Home, in this case, is the integrated health team.

Individual profiles for patients, health care providers, and clinical trial organizations can be developed from here for selecting health care providers most likely to refer, patients most interested in clinical trials, and clinical trial organizations and pharmaceutical companies that will want to refine and perfect the desired population set based on the intelligence of the Hub 150. Hub 150 communications occur within the safety of the electronic firewall 154. All communications between the Hub engine 150 and its databases 156 are secure and HIPAA Compliant.

The Hub Database 156 stores all matches by the Hub engine 150. These records are used for the management of confidentiality, historical responsibility, and developing further intelligence in the Hub's 150 algorithms and filters.

Data Feeds from the published Clinical Trials databases 160 are electronic links to publicly available Web sites. These sites define: criteria, timing, logistics, and geographical considerations for current and future clinical trials. Data Feeds from our proprietary Clinical Trials Database 160 provide the Hub 150 with an internal and proprietary source of information from an integrated Clinical Trials database 160.

The Clinical Trials Database 160 manages the proper selection of Clinical Trials, their information and the coordination of updates and notifications. It provides the Hub 150 with a unique intelligence as it monitors the criteria for thousands of Clinical Trials and can derive patterns and insight.

The Platform Web Applications 170 perform pre-processing of information and quality checks prior to notifying a HCP of a potential patient/trial match. This technology also structures the information into a deliverable format to the physician or other stakeholder. We pre-process all potential candidate subject/trial matches before they move to the HCPs for patient notifications. The pre-processing step involves employing inclusionary and exclusionary factor algorithms to determine what gets filtered out. Preprocessing and Quality Checks 170 are done prior to any information deliveries.

This is done with a combination of software tools. Examples of algorithm criteria used for filtering include: propensity of subject to enroll based on history of participation, clinical matching, geographical implications (there may be population studies of a specific region). These filters will also have the capability to identify trends in the population by the information being reported and captured. As an example of how this would work, a virus such as H1N1 (swine flu) could be detected across the map and also mapped to areas of highest concentration or geographical progression. There is a spatial-temporal aspect to this data as it is time stamped and geographically coded. This allows for historical reviews of episodes and trends as well as geographic and demographic perspectives. It can also be used to create statistically valid clinical demographics.

Figure 12:
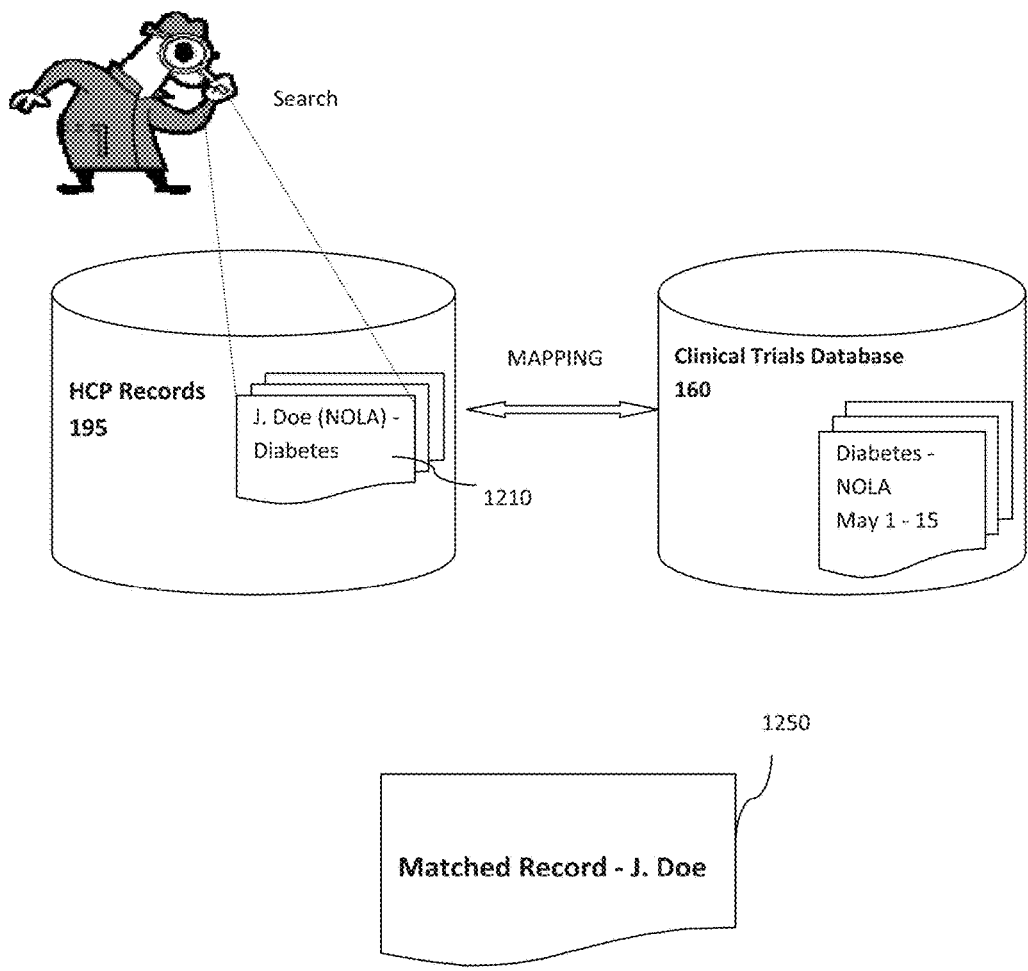
FIG. 12 shows an exemplary illustration of a manner in which clinical trial subjects can be identified, according to an embodiment of the present invention.

FIG. 12 shows an illustrative example of one method for identifying subjects for participating in clinical trials, according to one embodiment of the present invention. We perform a search on a HCP's Electronic Health Records Database 195 to extract patient records 1210 (subject to HIPAA rules). Then we map the patient records 1210 from the HCP database 195 to any clinical trials from the Clinical Trials Database 160 to match a patient record 1210 to a listed current or future clinical trial. In this example shown in FIG. 12, we find a match 1250 with a patient record 1210 for J. Doe from New Orleans, La. to a clinical trial for a diabetes drug scheduled for May in New Orleans. The matching can be performed using known methods, such as keyword match.

Electronic Mail Alerts 180 are generated for delivery in a number of secure and HIPAA compliant methods maintaining the patient-doctor confidentiality. These are sent directly to the HCP whose responsibility it is to notify, or not, their patient of a potential clinical trial that would be of benefit to them. Email alerts 180 go out to patient's HCPs after pre-validation from our team. The platform will support email, SMS (Short Message Service) and third-party software integration, among others, for match notifications. An API (application program interface) is also provided for Data Sharing services.

The Patient/Health Care Provider Feedback Loop 190 is a key aspect of the adaptive property of the invention. Within this loop 190, the HCP "meets" (in person, within chat room, or by video) with the patient to discuss the 'matched trial' and interest to proceed or not. If there is interest, the HCP provides the supporting information and instructions on how to register. A unique identifier is assigned to the subject in order to track the subject through the trial and beyond for proper management, compensation, and follow-up. The subject reviews the clinical trial details and determines the next step, perhaps contacting the Clinical Trial Organization to enroll. The subject is encouraged to provide feedback which is routed back into the Hub 150 for use in refining the selection and administration process.

Figure 2:
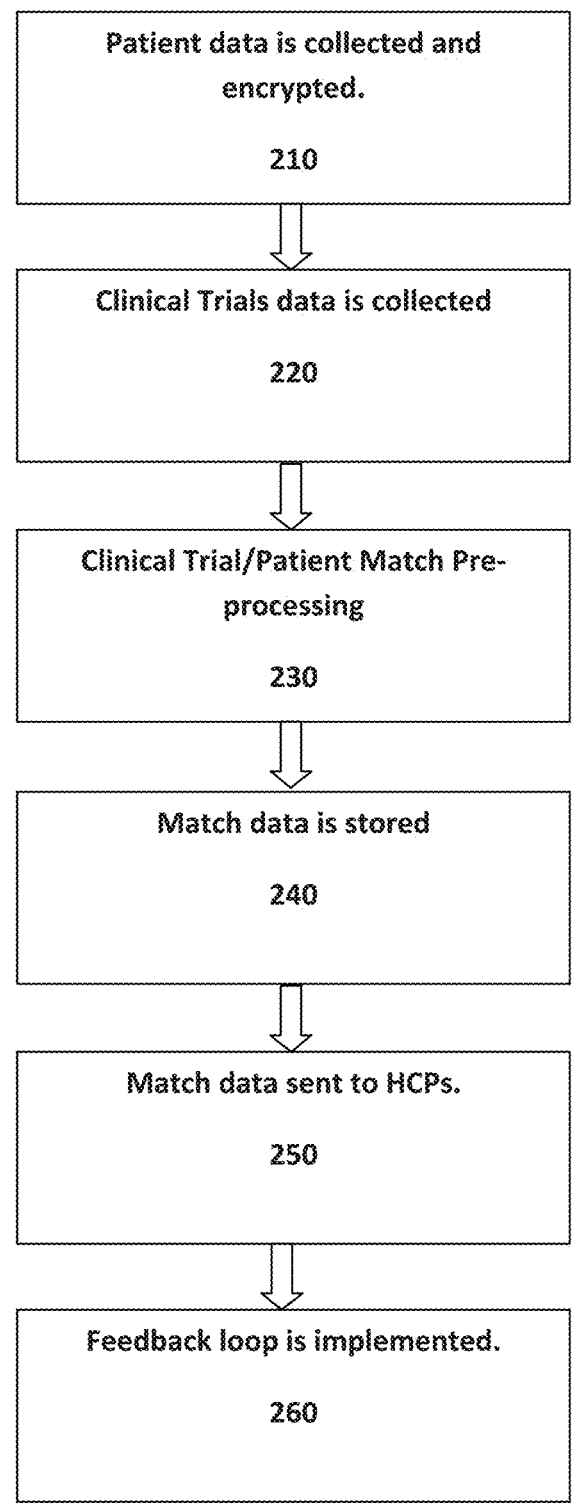
FIG. 2 is a flowchart of a method according to an embodiment of the invention.

Referring now to FIG. 2, we show a high-level flowchart 200 of a method for identifying subjects for clinical trials, according to an embodiment of the present invention. The method begins at step 210 with the collection of patient data 110. We collect patient data 110 from multiple sources and in varying formats. For example, patient data 110 may be input via voice data from partner Call Centers 120 as previously discussed. A partner Call Center 120 receives patient data 110 from a subject contacting the Call Center 120 to request medical advice regarding a health concern. The patient data 110 must be encrypted to ensure privacy.

In step 220 we continuously collect data pertaining to clinical trials, simultaneously with the patient data 110. This data is available from clinical trial organizations such as http://www.clinicaltrials.gov in the form of data feeds. It is important to keep up to date with government safeguards and protocols.

In step 230 we perform pre-processing 170 of the match. This includes feeding the potential match data into an algorithm and then employing a filter tool to further refine the selections. We first determine a plurality of parameters to consider for both the subject and the clinical trial. We assign weighted values to the parameters with a higher weight given to those parameters we determine are most important; likewise we assign a lower weight to those parameters we feel are less important in determining the likelihood of a match. We derive the importance of a factor based on what we have learned from our training data. For example, assume we have learned that younger patients in the United States are more likely to participate in clinical trials and that payment is a great inducement to them. We therefore assign a higher weight to a patient aged under thirty and we also assign a higher weight to a clinical trial that pays its subjects. Another example is: a patient with repetitive visits or communications with their oncologist would be securely identified to their HCP as a potential candidate for an existing trial.

In step 240 we store the match data in the Hub database 156. The match data not only provides the information we need to match potential subjects with trials, but it also provides a learning platform. We constantly refine and update the match pre-selection process by feeding match data as training data into a learning tool.

In step 250 we transmit the match data to the HCP through secure channels. We can transmit the data by email alerts or any other secure transmission format.

In step 260 we implement the feedback loop 190. We ask the HCP to provide feedback about the patient's decision and any other concerns/issues that need to be addressed. The HCP discusses the clinical trial with the subject and receives an indication from the subject about the subject's inclination to participate. If the subject decides to move forward and authorizes contact, we provide the clinical trial information, which includes a survey about the process.

Figure 3:
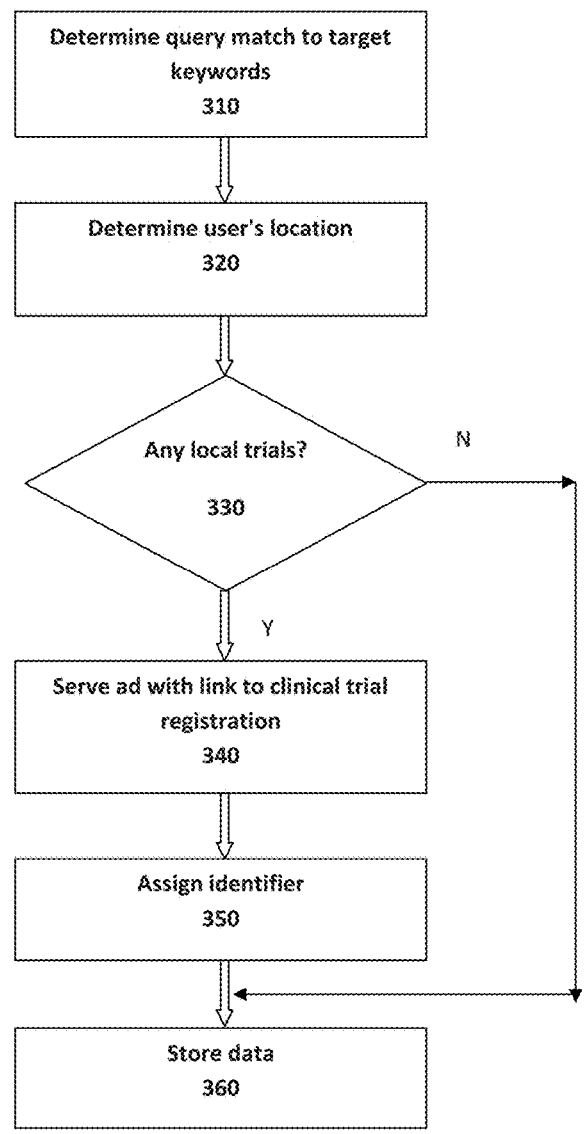
FIG. 3 is a flowchart of a method according to another embodiment of the present invention.
Figure 4:
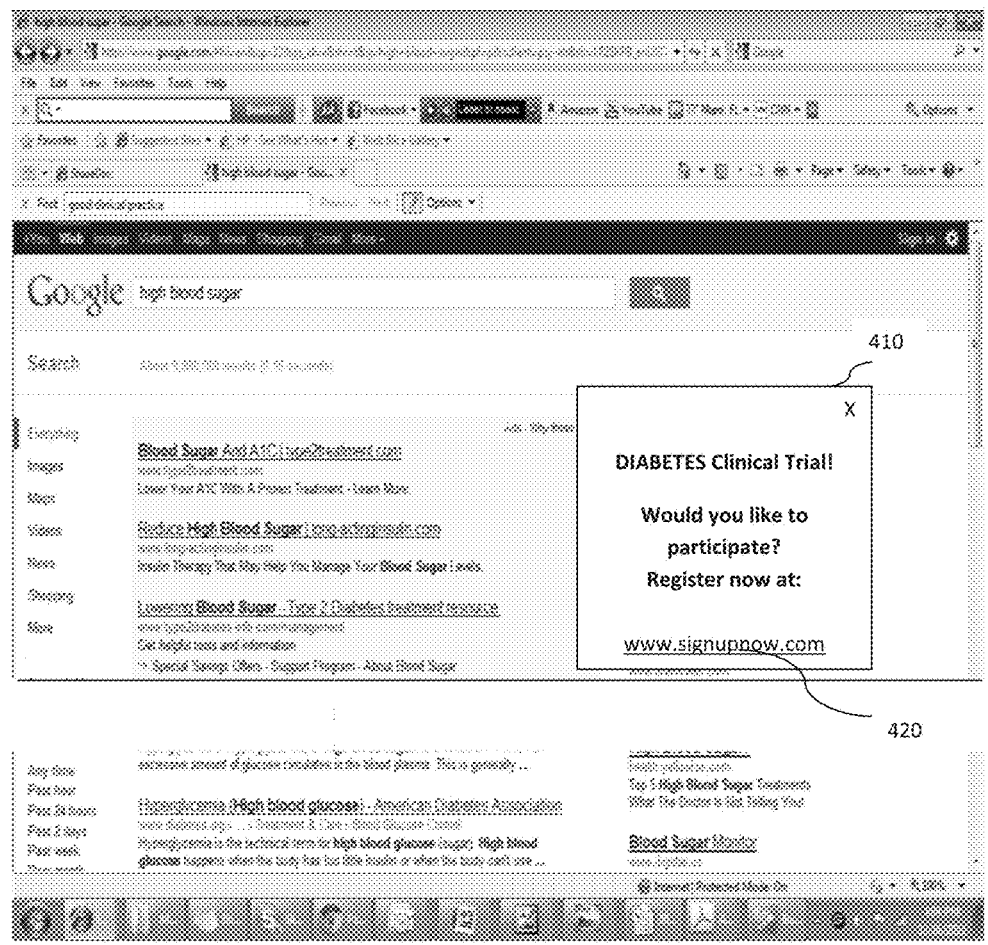
FIG. 4 shows an exemplary method of soliciting subjects for clinical trials, according to an embodiment of the present invention.

Up to this point, we have discussed one method of identifying subjects for clinical trials. In another embodiment of the present invention, we actively solicit subjects. Referring now to FIG. 3, we provide an exemplary method of soliciting subjects for clinical trials. With the immense amount of information available on the Web today, and the frustrating inefficiencies in health care, it is no wonder that people often turn to the Internet to answer their health questions. Web sites such as www.WebMD.com are popular because they are easy to navigate and provide up-to-date generalized information on a vast array of health issues. A subject has only to access the Internet through a Web browser and type in a search term. For this example, we assume that the subject has input a search query of "high blood sugar" into a search engine. Through a partnership with a web service provider (such as WebMD), we are able to receive this query term. This opens a channel for automatic linking and proactive advertizing of the service.

Figure 6:
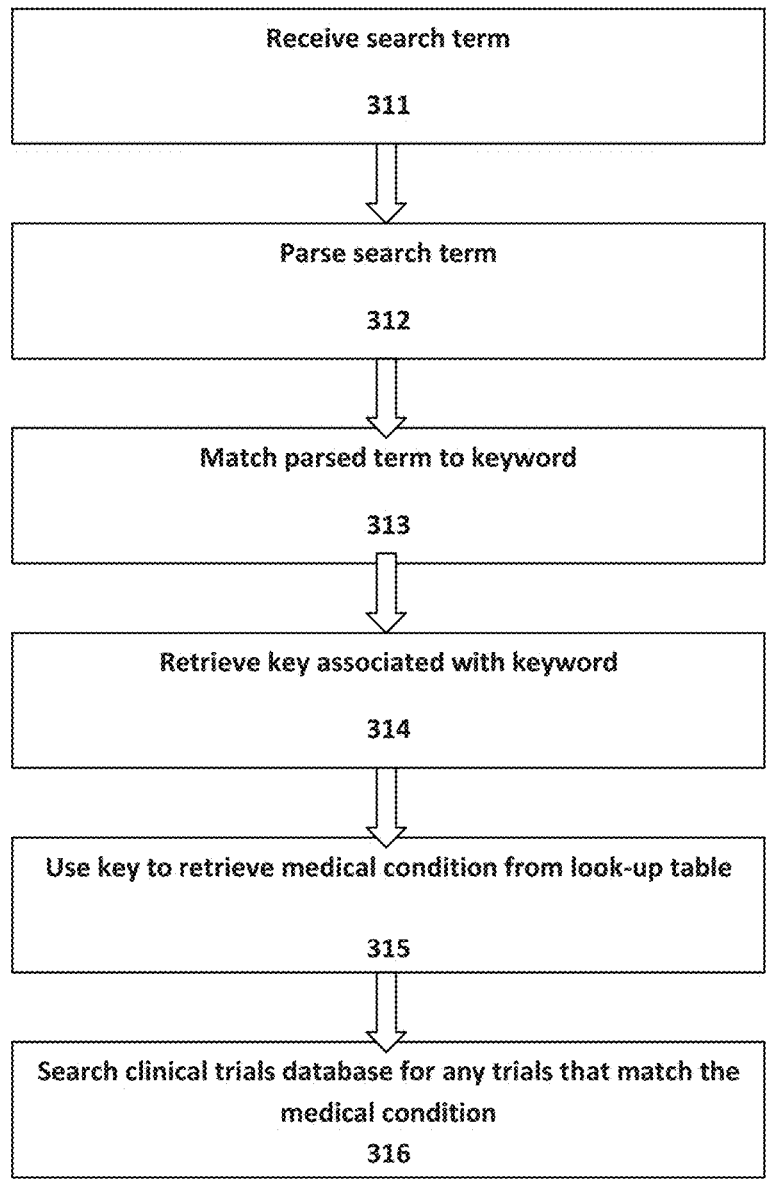
FIG. 6 is a flowchart of the method for matching search terms to clinical trials, according to an embodiment of the present invention.

In step 310 we determine if the input query term matches our pre-defined target keywords, such as "blood sugar," "high blood sugar," "diabetes," and the like. If there is a match to a target keyword, we query a look-up table to map the target keyword with a listing of diseases and other medical conditions. In this case, the look-up table maps the target keyword term "blood sugar" to the disease "diabetes" from our look-up table (shown in FIG. 7). In FIG. 6 we elaborate on this step.

In step 320 we determine the subject's location. This is accomplished through known geographical identifiers such as cookies and Web site registration profiles, phone numbers, and the like. Once the subject's location is known, in step 330 we are able to determine if there are any clinical trials related to the selected medical condition (diabetes) within a reasonable commute of the subject's location. We can establish a threshold distance from the subject's location. Any trials beyond that threshold distance are not considered "local."

If it is determined that local clinical trials are available, then in step 340 we render and serve the target ad to the subject in the form of a window, box, page, or banner. By "available" we mean a trial that is still open for registration or that is scheduled to occur within the near future. Referring now to the example shown in FIG. 4, the ad 410 may be served directly onto the search results page (SRP) 400 and will contain a link 420 to a URL providing information about the clinical trial and an on-line registration form.

In step 350 we assign a unique identifier to the subject. This unique identifier will identify the subject within the system 100 and will remain associated with the subject through the trial and any follow-up. In step 360 we store the data for future use as training data. The identifier is assigned at the time there is a match between trial and subject in the system. This triggers the process of notification of HCP and related documentation. An identifier is assigned to the subject prior to their decision to participate or not in the trial. This is required as the decision by the subject happens after consultation with their HCP. Information on subjects that did not decide to participate on the trials is kept for statistical studies. All of this information is stored anonymously, as per HIPAA.

Matching.

Referring now to FIG. 6 we show a flowchart of step 310 of the flowchart of FIG. 3 "Determine query match to target keywords." In step 311 we receive the search term from a web service provider such as WebMD. Alternately, we can access the search term from our proprietary website, or other means. In step 312 we parse the search term and remove any extraneous characters. In parsing the search term 710, we remove any extraneous characters (such as a question mark) from the term and separate the words because it may be necessary to use a portion of the search term, depending on what the user entered. Then in step 313 we match the parsed term to a target keyword from a keyword database of medical terms. If we find a match, in step 314 we retrieve the identifier, or key, associated with the keyword. We use that key to retrieve its associated medical condition from a look-up table in step 315. Using that listed medical condition, we then search for any clinical trials for that condition in the clinical trials database 160.

Look-Up Tables.

Figure 7:
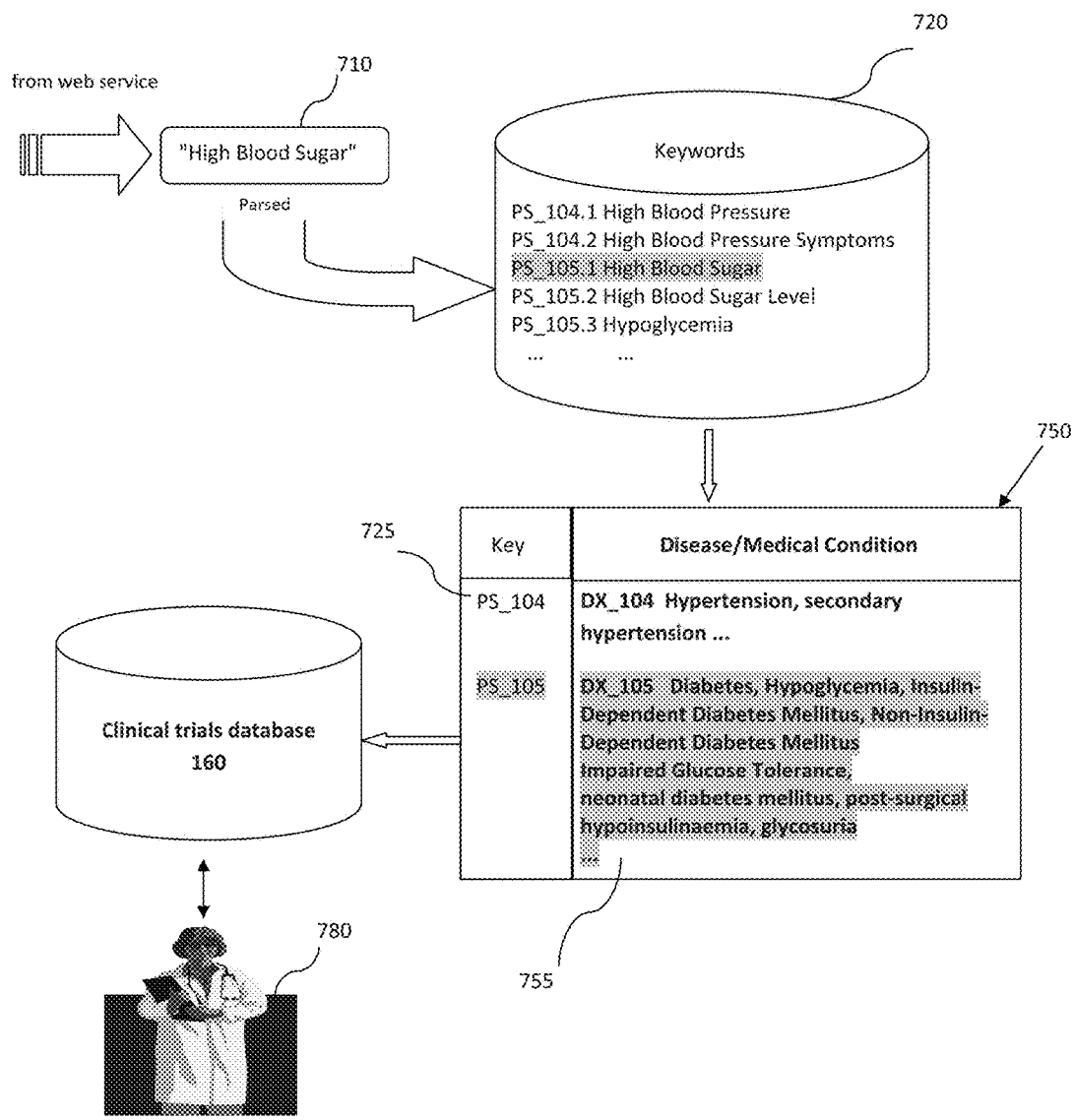
FIG. 7 is an exemplary look-up table, according to an embodiment of the present invention.

FIG. 7 provides a simplified illustration of the process of FIG. 6. After parsing the search term 710 we match the parsed term to a target keyword 725 from a keyword list 720. The keyword list 720 can be a database or a group of databases and can be kept locally or remotely. In this example the search term "High Blood Sugar" exactly matches the target keyword "high blood sugar" but this will not always be the case. In some cases, only a portion of the search term 710 will match a target keyword 725.

Using the target keyword 725 (or in this case an identifier associated with the target keyword 725) we look up the related medical condition 755 in the look-up table 750. The related medical condition 755 may or may not be associated with a clinical trial. We determine this by searching the clinical trials database 160 for the related medical condition 755. It should be noted that the target keywords 725 and the medical conditions 755 can be entered with classifiers from the ICD ("International Statistical Classification of Diseases and Related Health Problems") and DSM ("Diagnostic and Statistical Manual of Mental Disorders"). If the clinical trials database 160 yields a result that is deemed to be a good match for the subject, the information is sent to the subject's HCP 780 who will then communicate the subject's decision and provide any necessary feedback.

Figure 8:
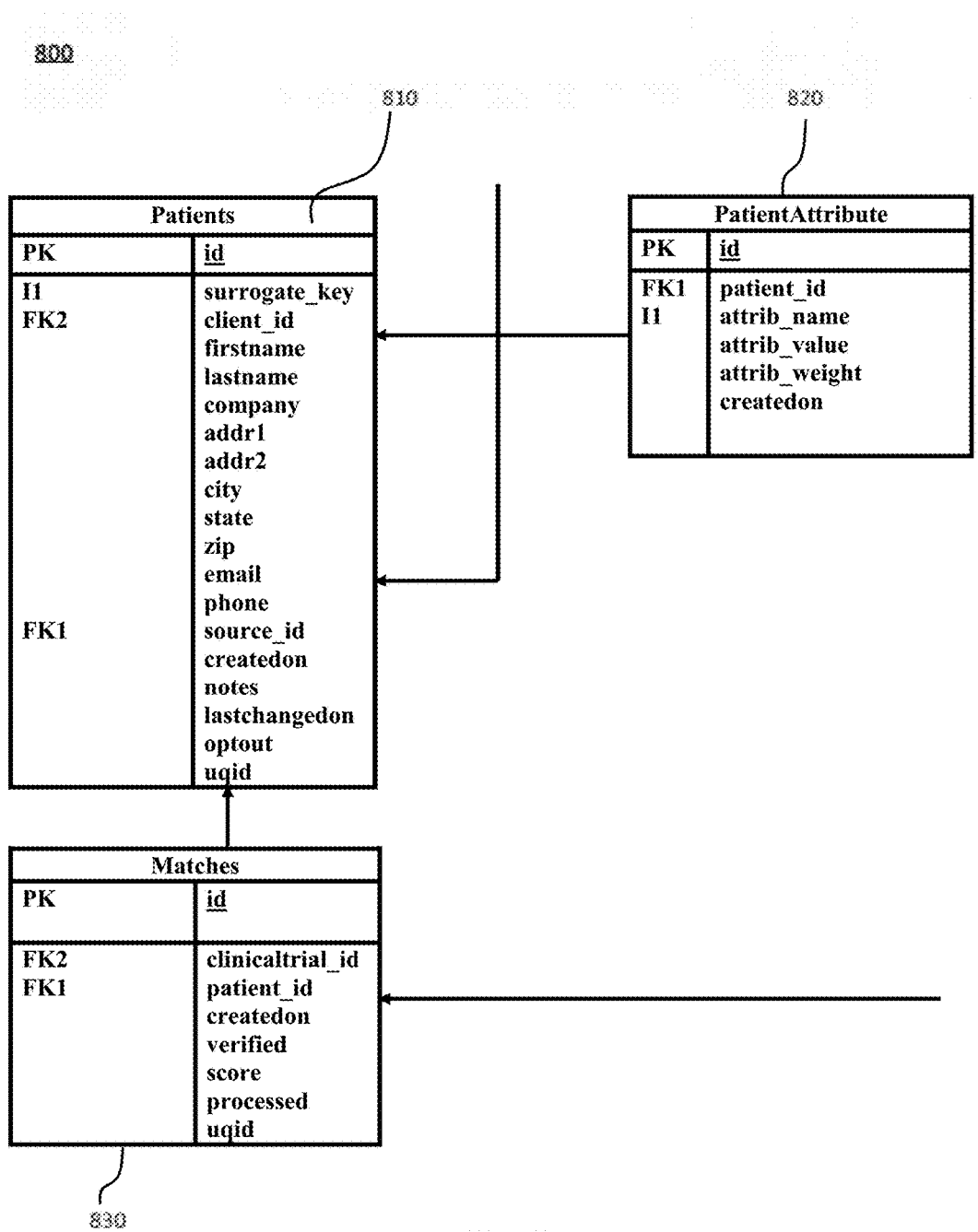
FIG. 8 depicts exemplary look-up tables matching a subject with a trial, according to an embodiment of the present invention.

FIG. 8 shows an example of using look-up tables to match patient attributes with a patient and then match that patient to a clinical trial. We show a look-up table 810 for patients and a look-up table 820 for patient attributes. A look-up table 830 for matches has the information for both the patient and the clinical trial.

The Simulator.

Figure 9:
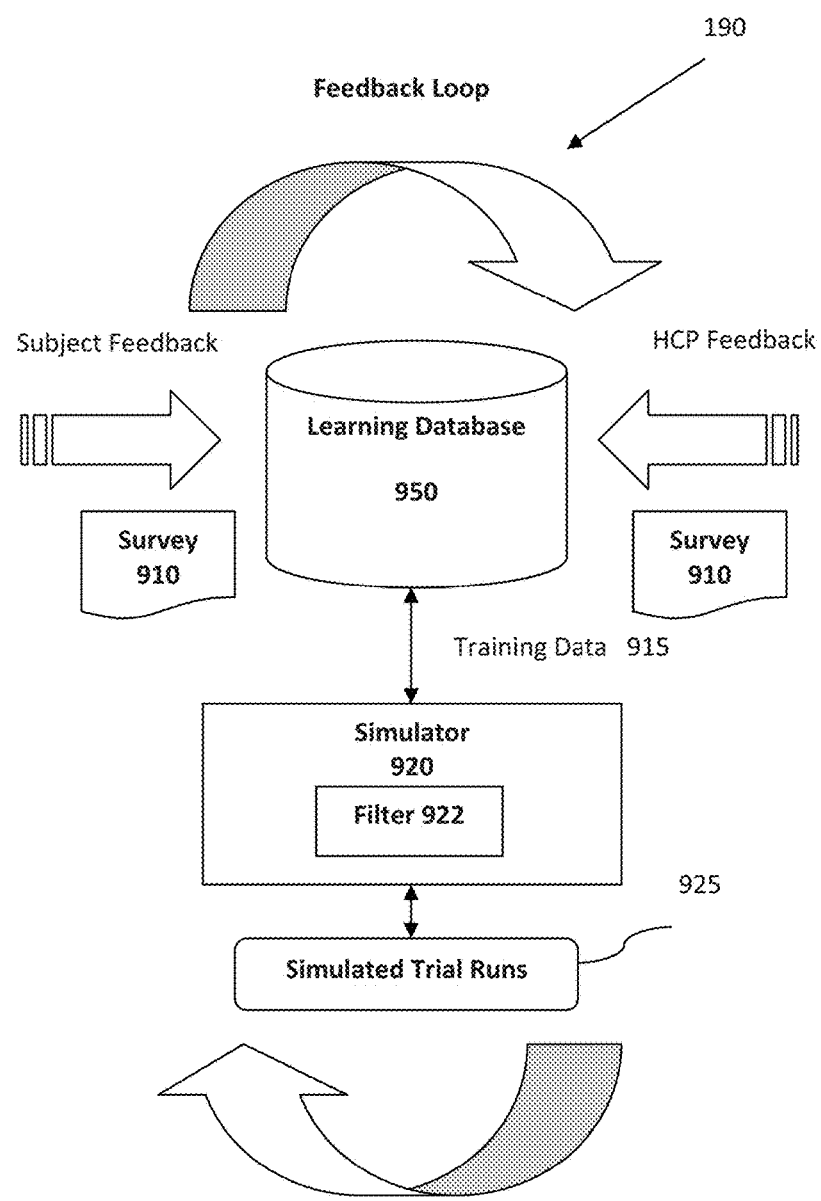
FIG. 9 is a simplified depiction of the simulator, according to an embodiment of the present invention.

FIG. 9 shows a simplified diagram of how the feedback loop 190 operates with respect to the simulator 920. After a clinical trial it is important to acquire as much feedback as possible, from both the HCP and the subject. We implement a 'Practice Web site' as a simulator 920. This simulator 920 allows the designer, administrator, or analyzer of a clinical trial to model questions, hypothesis, and conditions before, during, or after the trial. This is done by leveraging the existing database of information in the system as a baseline where variables can be changed, greater precision can be sought, or contextual mapping to previous or related trials can be performed. This provides a level of intelligence not available through current paper models or non-integrated electronic systems.

Within this simulator 920, we can adjust all of the filtering criteria/filters 922 to match either the pre-defined criteria from a clinical trial or use our analytics capabilities to provide greater insight beyond what is requested. This provides greater depth, inclusion of a greater number of weighted variables, and a new dimension of analysis.

For instance; we can adjust age, gender, and location with finer grain modeling against demographic studies and their correlation to disease types. We can validate clinical trial assumptions before the trial is deployed by matching to our existing database 160. We can validate results from trials based on our historical database comparisons and identify inconsistencies and areas for further analysis. The concept here is that we can iterate on a filtering scheme and reprocess the information, looking for more unique trends. This changes the dynamics from coarse to fine grade analysis, thereby providing higher value (precision) to the selection process and insight to the user of the system.

From these weighted metrics we further refine the selections by applying a filter 922 to the selections. The data used in the learning process is metadata (the data about the data). From our filtering methods we extract trends; these can be used to baseline given criteria. These are further used to define a higher level of insight than one-dimensional demographics. With every clinical trial, the system learns by capturing success and failures of data. For instance: subjects with a given gender/age group were more likely to respond to trials with a given criteria. This can further be enhanced by capturing direct information from the subjects about their feedback on process, interests, and recommendations. With this information, a greater learning dimension is added.

A survey 910 is a useful way to gather feedback. The feedback is entered into the learning database 950 which outputs training data 915. This training data 915 is fed into the simulator 920 which performs simulated trial runs 925. The simulator 920 is any computer device or group of networked computing devices that is configured according to an embodiment of the present invention. Data from the simulated trial runs 925 is returned to the simulator 920 and also stored in the database 950.

Figures 10, 11:
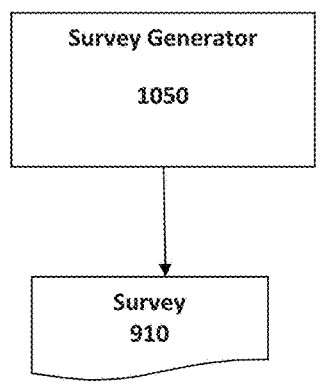
FIG. 10 is a simplified block diagram of a survey generator, according to an embodiment of the present invention.
FIG. 11 shows a simplified depiction of an on-line registration form, according to an embodiment of the present invention.

FIG. 10 shows a survey generator 1050 which is also part of the feedback loop 190. The survey generator 1050 prepares the surveys 910 which are provided to trial subjects, trial coordinators, and health care providers. Feedback from the survey 910 is stored in the learning database 950 so that the process can be continually improved. The surveys 910 can be customized with the data collected from the participants.

FIG. 11 shows a simplified depiction of an on-line registration form 1100 for a subject interested in a clinical trial. This on-line form 1100 can be presented as a site accessed from the ad 410 shown in FIG. 4 that is presented on a search results page. The registration form 1100 at a minimum must collect the subject's contact information (email address, phone, address) for further follow-up, if necessary. The subject provides this information and then receives a confirmation. Any required follow-up can be done automatically from within the system.

Monetization.

It is contemplated that clinical trial organizations, pharmaceutical companies, medical product companies, and/or health care providers are willing to pay for a completely automated system to match subjects with clinical trials. The matching service could be provided as a subscription service (monthly fee, yearly fee), or on a "per hit" basis, meaning that the company would pay only in the event of a successful match.

It is further contemplated within the spirit and scope of the invention that a charge for providing and monitoring registrations could be billed separately or included in a subscription service. Moreover, we contemplate that the survey and feedback processing can also be a separate charge or provided with a subscription service.

What we have discussed here is a system that can be completely automated, from an initial contact with a subject, through completion of trial and post-trial follow-up.

Figure 5:
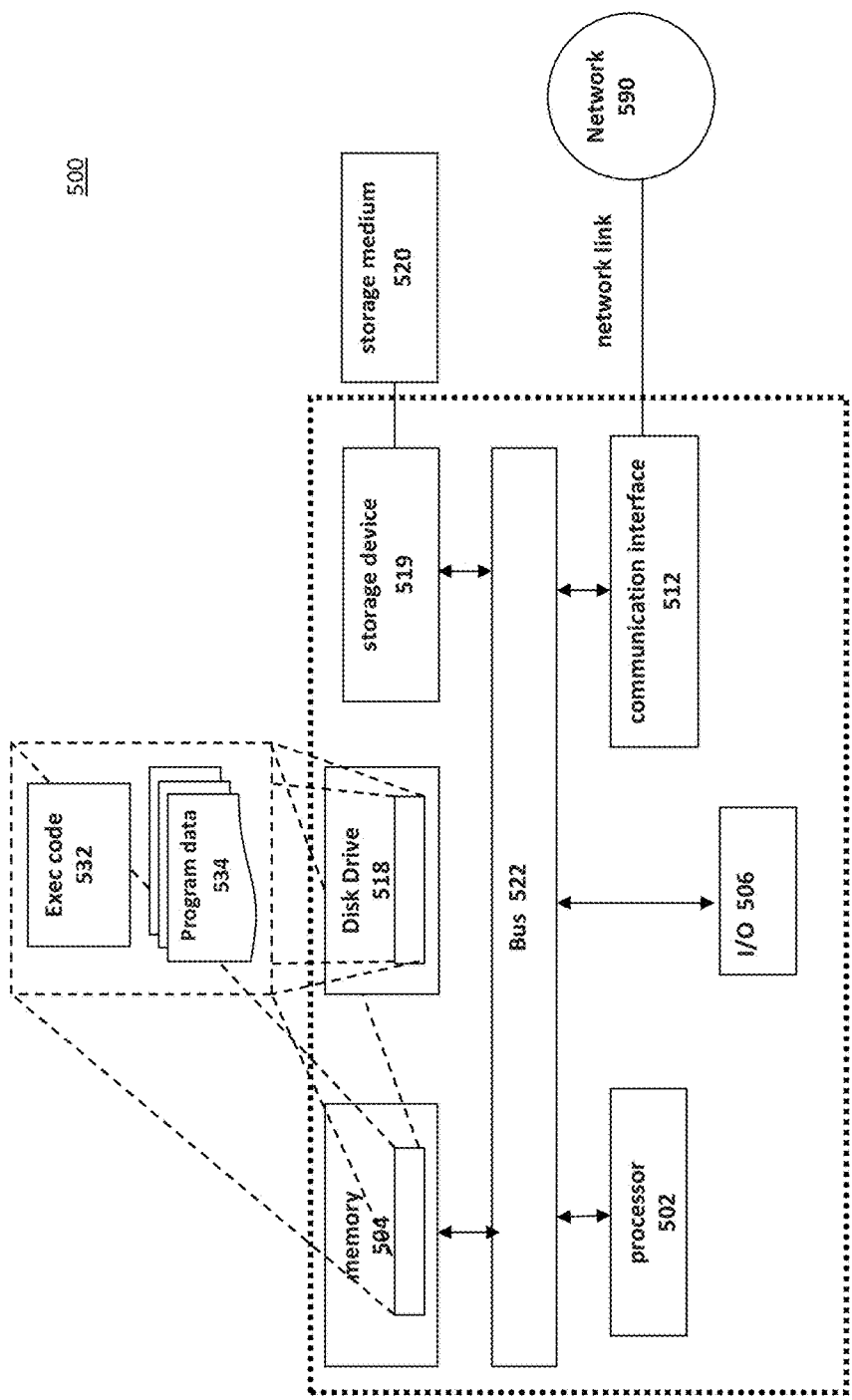
FIG. 5 is a high level block diagram showing an information processing system configured to operate according to an embodiment of the present invention.

FIG. 5 Hardware Embodiment.

Referring now to FIG. 5, there is provided a simplified pictorial illustration of an information processing system 500 for identifying subjects for clinical trials, in which the present invention may be implemented. For purposes of this invention, computer system 500 may represent any type of computer, information processing system or other programmable electronic device, including a client computer, a server computer, a portable computer, an embedded controller, a personal digital assistant, and so on. The computer system 500 may be a stand-alone device or networked into a larger system. Computer system 500, illustrated for exemplary purposes as a networked computing device, is in communication with other networked computing devices (not shown) via network 510. As will be appreciated by those of ordinary skill in the art, network 510 may be embodied using conventional networking technologies and may include one or more of the following: local area networks, wide area networks, intranets, public Internet and the like.

In general, the routines which are executed when implementing these embodiments, whether implemented as part of an operating system or a specific application, component, program, object, module or sequence of instructions, will be referred to herein as computer programs, or simply programs. The computer programs typically comprise one or more instructions that are resident at various times in various memory and storage devices in an information processing or handling system such as a computer, and that, when read and executed by one or more processors, cause that system to perform the steps necessary to execute steps or elements embodying the various aspects of the invention.

Throughout the description herein, an embodiment of the invention is illustrated with aspects of the invention embodied solely on computer system 500. As will be appreciated by those of ordinary skill in the art, aspects of the invention may be distributed amongst one or more networked computing devices which interact with computer system 500 via one or more data networks such as, for example, network 510. However, for ease of understanding, aspects of the invention have been embodied in a single computing device—computer system 500.

Computer system 500 includes processing device 502 which communicates with an input/output subsystem 506, memory 504, storage 510 and network 590. The processor device 502 is operably coupled with a communication infrastructure 522 (e.g., a communications bus, cross-over bar, or network). The processor device 502 may be a general or special purpose microprocessor operating under control of computer program instructions 532 executed from memory 504 on program data 534 such as patient data 110. The processor 502 may include a number of special purpose sub-processors such as a comparator engine and filter, each sub-processor for executing particular portions of the computer program instructions. Each sub-processor may be a separate circuit able to operate substantially in parallel with the other sub-processors.

The memory 504 may be partitioned or otherwise mapped to reflect the boundaries of the various memory subcomponents. Memory 504 may include both volatile and persistent memory for the storage of: operational instructions 532 for execution by CPU 502, data registers, application storage and the like. Memory 504 preferably includes a combination of random access memory (RAM), read only memory (ROM) and persistent memory such as that provided by a hard disk drive 518. The computer instructions/applications that are stored in memory 504 are executed by processor 502. The computer instructions/applications 532 and program data 534 can also be stored in hard disk drive 518 for execution by processor device 502.

Those skilled in the art will appreciate that the functionality implemented within the blocks illustrated in the diagram may be implemented as separate components or the functionality of several or all of the blocks may be implemented within a single component. For example, the functionality for the filter may be included in the same component as the comparator. The I/O subsystem 506 may comprise various end user interfaces such as a display, a keyboards, and a mouse. The I/O subsystem 506 may further comprise a connection to a network 590 such as a local-area network (LAN) or wide-area network (WAN) such as the Internet.

The computer system 500 may also include a removable storage drive 519, representing a CD-ROM drive, a magnetic tape drive, an optical disk drive, and the like. The removable storage drive 519 reads from and/or writes to a removable storage unit 520 in a manner well known to those having ordinary skill in the art. Removable storage unit 520, represents a floppy disk, a compact disc, magnetic tape, optical disk, CD-ROM, DVD-ROM, etc. which is read by and written to by removable storage drive 519. As will be appreciated, the removable storage unit 520 includes a non-transitory computer readable medium having stored therein computer software and/or data.

The computer system 500 may also include a communications interface 512. Communications interface 512 allows software and data to be transferred between the computer system and external devices. Examples of communications interface 512 may include a modem, a network interface (such as an Ethernet card), a communications port, a PCM-CIA slot and card, etc. Software and data transferred via communications interface 512 are in the form of signals which may be, for example, electronic, electromagnetic, optical, or other signals capable of being received by communications interface 512.

In this document, the terms "computer program medium," "computer usable medium," and "computer readable medium" are used to generally refer to both transitory and non-transitory media such as main memory 504, removable storage drive 520, a hard disk installed in hard disk drive 518, and signals. These computer program products are means for providing software to the computer system 500. The computer readable medium 520 allows the computer system 500 to read data, instructions, messages or message packets, and other computer readable information from the computer readable medium 520.

Therefore, while there has been described what is presently considered to be the preferred embodiment, it will understood by those skilled in the art that other modifications can be made within the spirit of the invention. The above description(s) of embodiment(s) is not intended to be exhaustive or limiting in scope. The embodiment(s), as described, were chosen in order to explain the principles of the invention, show its practical application, and enable those with ordinary skill in the art to understand how to make and use the invention. It should be understood that the invention is not limited to the embodiment(s) described above, but rather should be interpreted within the full meaning and scope of the appended claims.

We claim:

1. A method of automatically matching a subject with an available clinical trial, the method comprising:
   using an input/output interface device performing:
      collecting patient data associated with the subject, wherein the patient data is collected from a voice transaction made with the subject via a web browser, wherein the voice transaction is made via a call made via a web page rendered by the web browser;
      identifying the subject based on the patient data collected from the voice transaction and based on a cookie file;

determining a first location of the subject based on the cookie file, wherein the first location is where the subject is currently located;

routing the call based on the cookie file and the web page that the call was made from;

parsing a search term received via the web browser, wherein parsing the search term comprises removing an extraneous character from the search term and separating each word in the search term from other words in the search term; and collecting clinical trial data from multiple sources;

using a processor device operably coupled to the input/output interface device, the processor device performing:

matching, based on the patient data collected from the voice transaction and the clinical trial data, the subject to a clinical trial scheduled in a second location accessible to the subject, wherein matching the subject to the clinical trial is further based on a health condition that is determined by matching the parsed search term to a target keyword having a key that is utilized to determine the health condition, wherein the second location is different from the first location where the subject is currently located, wherein the matching is performed independent of the subject requesting the clinical trial; and using the input/output interface device to perform:

notifying a health care provider associated with the subject about the clinical trial;

receiving a response; and conducting, by utilizing a simulator including a group of networked computing devices, a simulated trial run for the clinical trial based on received feedback associated with the clinical trial.

2. The method of claim 1, wherein collecting the patient data comprises obtaining the voice transaction via a chat feature provided on a web site.

3. The method of claim 1, wherein collecting the patient data comprises receiving an on-line inquiry from a web site.

4. The method of claim 1, wherein notifying the health care provider comprises transmitting an electronic message.

5. The method of claim 1, further comprising:
receiving an indication that the subject matched to the clinical trial agrees to participate in the clinical trial;
assigning a unique identifier to the subject;
receiving information from the subject; and
storing the information received from the subject for use as training data.

6. The method of claim 1, further comprising:
receiving an indication that the subject matched to the clinical trial subject declines to participate in the clinical trial;
soliciting a reason why the subject declined to participate;
storing the reason for declining to participate; and
inputting the reason for declining to participate as training data in a learning tool.

7. The method of claim 1, wherein matching the subject to the clinical trial comprises:
assigning weighted values to subject parameters;
assigning weighted values to clinical trial parameters;
running, based on the weighted values assigned to the subject parameters and based on the weighted values to the clinical trial parameters, an algorithm to generate a primary selection of matched subject/trial pairs; and
applying a filter to further refine the primary selection to generate a secondary selection.

8. The method of claim 1, further comprising:
providing a survey to one or more of: the subject, the health care provider, or an organization conducting the clinical trial;
receiving the feedback from the survey; and
inputting the feedback from the survey as training data in a learning tool.

9. A distributed computing system for identifying a subject for a clinical trial, the system comprising:
a memory with computer-executable instructions stored therein;
a processor that executes the instructions to perform operations, the operations comprising:
collecting patient data associated with the subject, wherein the patient data is collected from a voice transaction made with the subject via a web browser, wherein the voice transaction is made via a call made via a web page rendered by the web browser;
identifying the subject based on the patient data collected from the voice transaction and based on a cookie file;
determining a first location of the subject based on the cookie file, wherein the first location is where the subject is currently located;
routing the call based on the cookie file and the web page that the call was made from;
parsing a search term received via the web browser, wherein parsing the search term comprises removing an extraneous character from the search term and separating each word in the search term from other words in the search term;
collecting clinical trial data from multiple sources;
matching, based on the patient data collected from the voice transaction and the clinical trial data, the subject to a clinical trial scheduled in a second location accessible to the subject, wherein matching the subject to the clinical trial is further based on a health condition that is determined by matching the parsed search term to a target keyword having a key that is utilized to determine the health condition, wherein the first location where the subject is currently located is different from the second location, wherein the matching is performed independent of the subject requesting the clinical trial;
receiving feedback from the subject regarding the clinical trial;
refining selection of the clinical trial based on the feedback;
notifying a health care provider associated with the subject about the clinical trial;
receiving a response; and
conducting, by utilizing a simulator including a group of networked computing devices, a simulated trial run for the clinical trial based on the received feedback associated with the clinical trial.

10. The distributed computing system of claim 9, further comprising:
a learning database for storing data about matched subject/trial pairs as training data; and
the simulator that utilizes the training data as input.

11. The distributed computing system of claim 9, wherein the patient data comprises subject health information and subject health concerns.

12. The distributed computing system of claim 11, wherein the patient data further comprises one or more of: lifestyle data, genomics data, environmental data, and demographic data.

13. The distributed computing system of claim 9, wherein the patient data comprises location data used to match the subject with the clinical trial scheduled in the second location accessible to the subject.

14. The distributed computing system of claim 9, further comprising:
   a survey generator producing customized surveys presented to one or more of:
   trial subjects, trial coordinators, and health care providers.

* * * * *